(12) United States Patent
Duva

(10) Patent No.: US 6,512,666 B1
(45) Date of Patent: Jan. 28, 2003

(54) HIGH CURRENT FILTER FEED-THROUGH CAPACITOR

(75) Inventor: Frank A. Duva, Carlsbad, CA (US)

(73) Assignee: Delware Capital Formation, Inc., Wilmington, DE (US)

(*) Notice: Subject to any disclaimer, the term of this patent is extended or adjusted under 35 U.S.C. 154(b) by 0 days.

(21) Appl. No.: 10/022,717

(22) Filed: Dec. 17, 2001

Related U.S. Application Data

(60) Provisional application No. 60/313,839, filed on Aug. 21, 2001.

(51) Int. Cl.[7] .......................... H01G 4/06; H01G 4/005
(52) U.S. Cl. ................... 361/321.2; 361/302; 361/303
(58) Field of Search ........................... 361/302, 321.2, 361/301.4, 303, 304, 306.3, 309, 313; 29/25.41, 25.03, 25.42

(56) References Cited

U.S. PATENT DOCUMENTS

| | | | |
|---|---|---|---|
| 2,389,420 A | | 11/1945 | Deyrup |
| 3,809,973 A | * | 5/1974 | Hurley ................... 29/25.42 |
| 4,450,502 A | | 5/1984 | Alexander |
| 4,556,929 A | | 12/1985 | Tanaka et al. |
| 5,319,517 A | * | 6/1994 | Nomura et al. ......... 252/519.12 |
| 5,333,095 A | | 7/1994 | Stevenson et al. |
| 5,334,411 A | | 8/1994 | Pepin |
| 5,345,361 A | * | 9/1994 | Billotte et al. ............. 29/25.03 |
| 5,347,423 A | * | 9/1994 | deNeuf et al. ............. 29/25.42 |
| 6,104,598 A | | 8/2000 | Duva |

* cited by examiner

Primary Examiner—Anthony Dinkins
(74) Attorney, Agent, or Firm—Christie, Parker & Hale, LLP

(57) ABSTRACT

An improved monolithic multilayer ceramic filter capacitor for use with implanted medical devices such as pacemakers and defibrillators. The capacitor includes a parallel stack of positive electrode plates that have sufficient current carrying capability to be directly connected in series with a lead wire from an implanted medical device. Therefore, the capacitor may be used for both filtering and pulsed energy transmission. High current capability is achieved through the use of interleaved electrode plates where the positive electrodes are connected in parallel, and where at least one of the positive electrodes is of sufficiently high conductor density to carry a majority of the current transmitted by the implantable medical device lead.

9 Claims, 2 Drawing Sheets

HIGH CURRENT FILTER FEED-THROUGH CAPACITOR

CROSS-REFERENCE TO RELATED APPLICATION(S)

This application claims priority from U.S. Provisional Patent Application No. 60/313,839 filed Aug. 21, 2001 now abandoned.

BACKGROUND OF THE INVENTION

This invention relates generally to improvements in ceramic filter capacitors of the type used for decoupling undesired interference signals from implantable medical devices such as defibrillators and pacemakers. More particularly, the invention relates to an improved feedthrough ceramic filter capacitor.

As typically constructed, a feedthrough filter capacitor used to suppress undesired electromagnetic interference ("EMI") signals along a pacemaker or defibrillator electrical lead has two or more sets of electrode plates embedded in a stacked spaced relationship within an insulative substrate. The stacked plates alternate between electrically positive plates and electrically negative or ground plates. Generally, the positive electrode plates are connected in parallel to the medical device electrical lead utilized to pass the desired electrical signals. In operation, the filter capacitor permits the passage of the relatively low frequency desired electrical signals, while shunting the relatively high frequency undesired electrical signals to a ground which is typically the conductive housing of the implanted medial device. Such devices typically have conductive housings formed from a biocompatible conductive alloy such as titanium. Preferably, the ground plates of the filter capacitor are directly coupled to the medical device housing to ensure against the entry of EMI signals to the interior of the device housing. The entry of any undesired EMI signals to the interior of the pacemaker, defibrillator, or other medical device may adversely effect the functioning of the device with significant adverse consequences to the health of the patient.

Multilayer ceramic capacitors of the type described above consist of a plurality of interleaved layers of conductive film and dielectric material. The conductive layers are formed by the deposition of a thick film metal paste or ink, commonly referred to as the electrode composition, over previously formed dielectric layers of ceramic oxide material.

The electrode composition is usually a dispersion of finely divided precious metal powders such as palladium, silver, gold, or platinum and mixtures thereof, in a binder, which is usually solely organic in nature. Dispersions of non-precious metals such as copper and nickel have also been found to have utility in electrode compositions. The binder is usually composed of a mixture of a polymeric resin which imparts viscosity to the composition and appropriate solvents for processing compatibility, particularly with respect to drying. Typical electrode composition metal concentrations range from about 40% to about 70% by weight, with the remainder being binder.

The dielectric layer is usually composed of finely divided oxide powders dispersed in a resin. Barium titanate and other oxides such as neodymium titanate and magnesium titanate are used. Additions are usually made to these oxides to control various electrical characteristics and particularly to maximize the dielectric constant. The resin is also present in the dielectric layer to facilitate the handling and deposition of electrodes on the layers.

Multilayer ceramic capacitors are manufactured by building up an interleaved configuration of electrode and dielectric layers, dicing individual parts out of the buildup and then subjecting the parts to a slow burnout or curing, then high temperature sintering. Burnout is done to remove the organic resin in the electrode and dielectric layers to avoid rapid outgassing and rupture of the layers. Sintering is done to a peak temperature to both densify the dielectric material to achieve physical strength, and to react the chemical constituents of the dielectric such that the desired electrical characteristics are achieved. During the sintering step, the powder grains in the electrode layers also densify so as to produce a continuous, electrically conductive metal film.

One common process for forming the interleaved structure of metal film and dielectric layers is referred to as the "dry stack process." In the dry stack process, the dielectric is cast into a tape from a slurry of dielectric powder, solvents, and pliable resins. An electrode layer is then deposited on the tape, typically using a screen printing process. Another layer of tape is placed over the dried electrode print, a subsequent electrode is printed on the tape, dried, and another tape is placed. This process is repeated until the number of layers desired is achieved. Once completed, metal ink/dielectric layers are cured and sintered as described above.

Although, ceramic capacitors of the type described above are in widespread use as filter capacitors for implantable medical devices, such capacitors have limited current carrying capability are therefore limited to parallel connections with the leads from the implanted medical device. However, recent advances in pacemaker and defibrillator technology have created a need for capacitors with enhanced EMI filtering capability. To achieve such capability it is necessary to connect the filter capacitor in series with the leads from the implanted medical devices. However, series connection creates an additional problem in that the series connected capacitor must be capable of carrying the full current load of the lead to which it is connected. Capacitors of prior art design are not able to carry the necessary currents in a package size small enough to be used with implantable pacemakers and defibrillators. Thus, there exists a need for a high current feedthrough capacitor that may be connected in series with the leads of implantable medical devices.

SUMMARY OF THE INVENTION

The present invention is an improved monolithic multilayer ceramic filter capacitor for use with implanted medical devices such as pacemakers and defibrillators. The new capacitor includes a parallel stack of positive electrode plates that, when combined, have sufficient current carrying capability such that they may be directly connected in series with a lead wire from an implanted medical device. Thus, the present invention capacitor may be used for both filtering and pulsed energy transmission from a device such as a defibrillator. This is in marked contrast with prior art capacitors which may be used for signal filtering only.

The present invention capacitor is capable of carrying high current through the use of interleaved electrode plates where the positive electrodes are connected in parallel, and where at least one of the positive electrodes is of sufficiently high conductor density to carry a majority of the current transmitted by the implantable medical device lead. Preferably, the high conductor density electrode is an external or surface electrode. With this design, the present invention capacitor may be produced in a smaller package than a conventional ceramic capacitor of equivalent current rating. Through the use of a high density surface electrode, the present invention capacitor allows for an increase in the number of internal electrode plates, thereby providing for increased capacitance and greater signal filtering capability, than would be achievable with a conventional ceramic capacitor of the same physical size and similar current carrying capacity. Other features and advantages of the invention will become more apparent from the following detailed description of the invention, when taken in conjunction with the accompanying exemplary drawings.

DETAILED DESCRIPTION OF THE INVENTION

Figure 1:
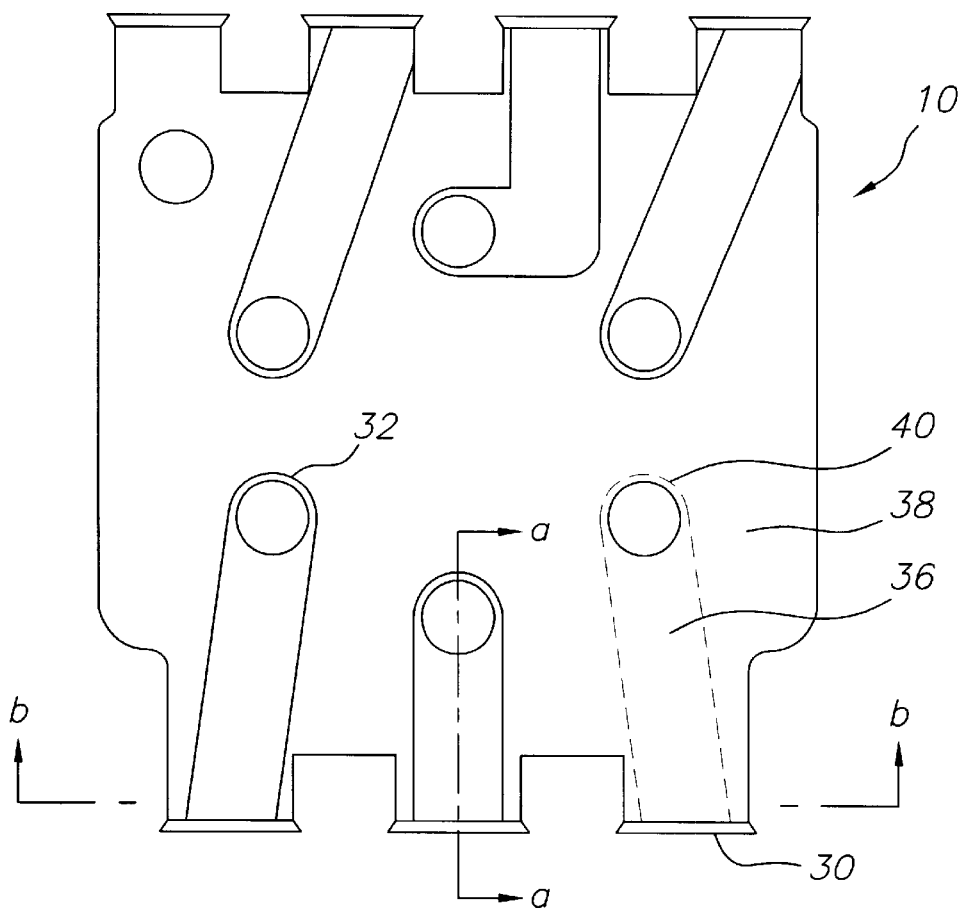
FIG. 1 is a top view, enlarged in scale, of an exemplary monolithic block of six capacitors in accordance with the present intention.
Figure 2:
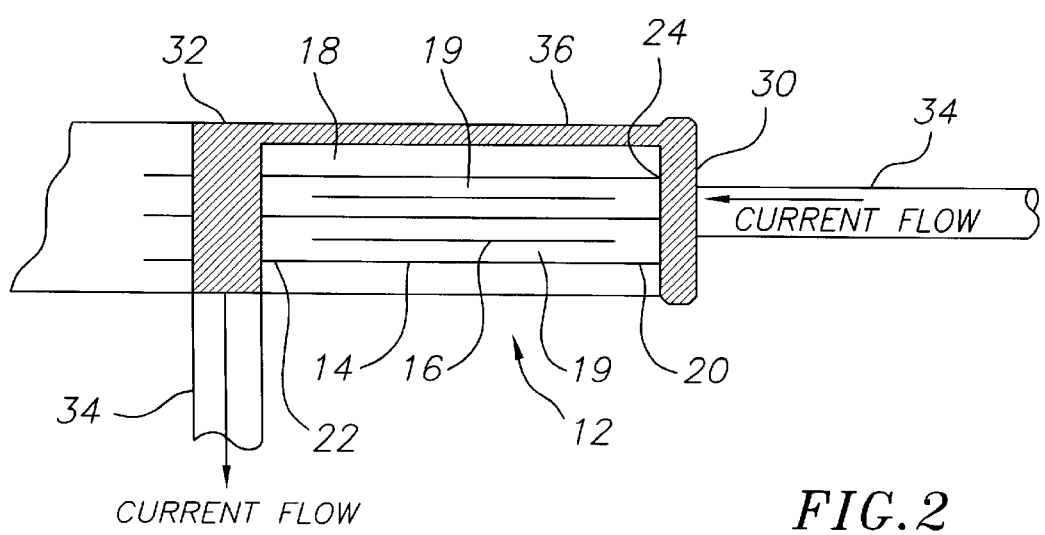
FIG. 2 is a schematic view, taken along the line a—a, of one of the capacitors of the monolithic block of FIG. 1.
Figure 3:
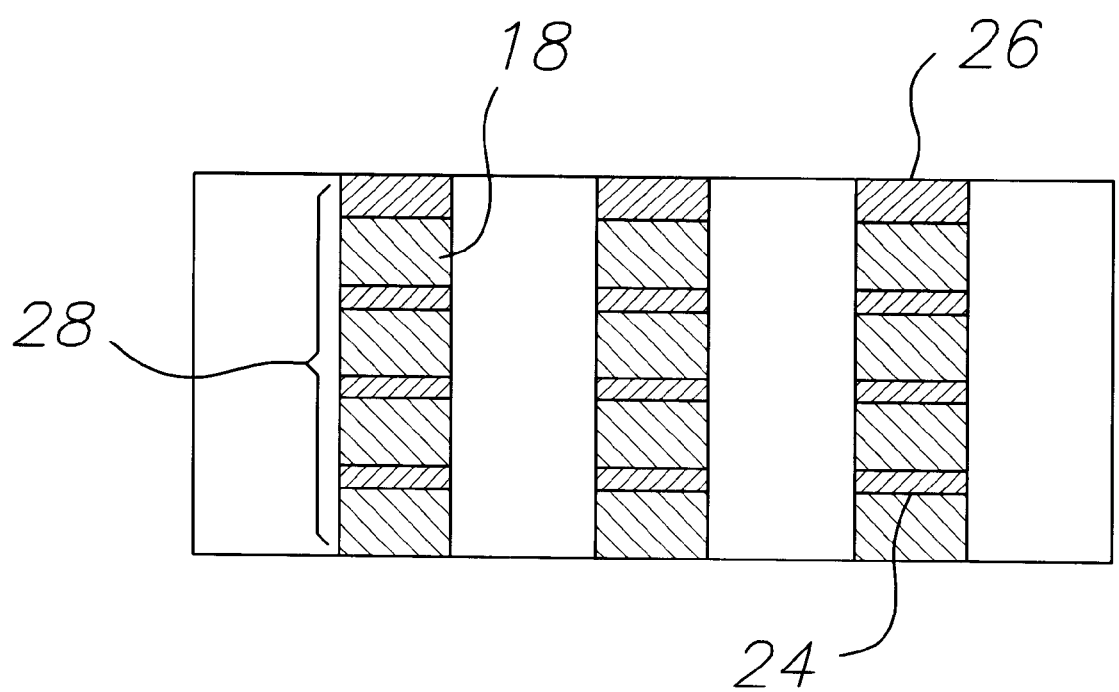
FIG. 3 is a sectional view, taken along the line b—b, of the monolithic block of capacitors shown in FIG. 1.

Although FIGS. 1–3 depict a monolithic block of six capacitors, the actual number of capacitors in the block is dependant on the number of lead wires used by a particular pacemaker, defibrillator, or other medical device. Therefore, the figures are meant to be exemplary only, as the actual number of capacitors will vary depending on the application. For simplicity, the following description refers to only a single capacitor. Those skilled in the art will understand that the principles described may be readily expanded to a plurality of capacitors.

Referring to FIGS. 1–3, the capacitor of the present invention 10 is constructed as a stack 12 comprising surface dielectric layers 18, intermediate dielectric layers 19, and positive and negative electrodes or plates, 14 and 16, interleaved with the intermediate dielectric layers. The negative and positive plates are generally rectangular in configuration and are typically disposed at right angles to each other. Each positive electrode plate has a first end 20 and a second end 22, and is surrounded by dielectric material except for an edge 24 of the first end which extends outwardly to a side 26 of the stack (FIG. 3). This formation leaves one side of the stack with a region 28 (FIG. 3) composed of alternating layers of exposed edges of positive plates and dielectric material. In this region, the first ends of all the positive electrodes may be electrically connected in parallel by forming a metalized pad 30 along the side of the stack. At the second ends of the positive electrodes, an internal hole 32 is drilled and filled with electrode material to electrically connect the second ends of the plates. With this construction, a lead wire 34 from a medical device (not shown) may be connected in series with the parallel connected stack of positive plates.

Due to the relatively high amperage carried in a typical medical device lead wire (about 35 amperes), the present invention capacitor 10 further includes a high density positive electrode or conductor 36, which is preferably formed on one of the surface dielectric layers 18 of the stack 12. The high density electrode is produced by milling or otherwise machining a slot 40 (best shown in FIG. 1) in the one of the surface dielectric layers of the capacitor. The slot is subsequently filled with electrode material to form the high current conductor 36. The high current conductor connects the internal positive electrode contact hole 32 with the metalized pad 30. Since current from the lead wire 34 will flow through the parallel stack of positive plates in proportion to the resistance of each plate, the majority of the current passing through the medical device lead wire 34 is carried by the comparatively high density or high resistance conductor 36, with the remainder being proportionately carried in the positive electrode plates 14 according to the resistence of each plate. The milled slot 40 which forms the high current conductor is of sufficient width and depth such that when filled with electrode material, the resulting conductor 36 will pass the required high current without overheating, arcing, or delaminating from the dielectric substrate. The above described capacitor construction allows for the transmission of medical device lead wire signals in series with the positive electrode plates 14 without fear of capacitor failure. Series transmission of medical device signals results in better filtering of undesired EMI than has heretofore been achievable.

The ground plates 16 of the present invention capacitor 10 are connected to a common ground which may be accomplished by conventional means known in the art. One approach, as used in the exemplary embodiment, is to form the ground plates at right angles to the positive plates 14 in such a manner that the positive and negative plates do not overlap at one end. With this construction, an internal hole may be drilled through the stack 12 in the area where the ground plates do not overlap the positive plates. The internal hole is subsequently filled with electrode material to electrically connect all of the negative plates. Alternatively, one end of the negative plates may extended to a side of the stack 12, whereupon the side may be metalized to electrically connect all of the ground plates. Other forms of plate termination are possible and known in the art.

An exemplary process for manufacturing the present invention capacitor comprises; casting dielectric in the form of tape produced from ceramic oxide powder through the use of a belt casting machine, screen printing electrode plates on the tape with electrode material in the form of thick film metal ink of typically precious metal composition, pressing and curing (burning out) the interleaved tape stack, and then sintering (heat fusing or laminating) the stack. The above process is commonly referred to as "dry stack" processing. Other methods such as "wet stack" processing are also suitable. After sintering, the slot 40 for the high density conductor 36 may be milled or otherwise formed into one of the surface layers of ceramic dielectric material and any internal electrode plate connection holes may be drilled. Subsequent, to these operations, the slot and holes are filled with electrode material, and any regions of exposed positive or negative electrodes may also be covered with metal ink. Next the stack is sintered for a second time to produce the finished capacitor. The slot 40 and other external features may be produced through laser or water-jet machining techniques which are known to those skilled in the art.

The present invention provides an improved filtering capacitor which allows for pulsed electrical energy from the leads of medical devices to be transmitted directly through the positive plates of the capacitor thereby improving the filtering of undesired EMI radiation, i.e. "electrical noise." The new capacitor is well suited for manufacture in monolithic ceramic form using existing equipment. While only the presently preferred embodiment has been described in detail, as will be apparent to those skilled in the art, modifications and improvements may be made to the device disclosed herein without departing from the scope of the invention. Accordingly, it is not intended that the invention be limited except as by the appended claims.

What is claimed is:

1. A high current multilayer ceramic capacitor comprising:
   a plurality of layers of a ceramic substrate;
   a plurality of electrodes interleaved with intermediate layers of the ceramic substrate;
   a high conductive density electrode formed on an exposed surface of a top or bottom layer of the substrate;
   means for electrically connecting alternating layers of electrodes to form a set of positive electrodes and a set of ground electrodes;
   wherein the high conductive density electrode is one of the positive electrodes; and
   wherein the high conductive density electrode is produced by forming a slot in the exposed surface of one of the surface ceramic layers and wherein the slot is filled with conductive material.

2. The capacitor of claim 1, wherein the slot is formed by machining the surface ceramic layer.

3. The capacitor of claim 2, wherein the method of machining is selected from the group consisting of laser or water jet machining.

4. A high current multilayer ceramic capacitor comprising:
   a plurality of layers of a ceramic substrate;
   a plurality of electrodes interleaved with intermediate layers of the ceramic substrate;
   a high conductive density electrode formed on an exposed surface of a top or bottom layer of the substrate;
   means for electrically connecting alternating layers of electrodes to form a set of positive electrodes and a set of ground electrodes;
   wherein the high conductive density electrode is one of the positive electrodes; and
   wherein the positive electrodes have first and second ends, each set of ends being electrically connected in parallel.

5. A high current multilayer ceramic capacitor comprising:
   a plurality of layers of a ceramic substrate;
   a plurality of electrodes interleaved with intermediate layers of the ceramic substrate;
   a high conductive density electrode formed on an exposed surface of a top or bottom layer of the substrate;
   means for electrically connecting alternating layers of electrodes to form a set of positive electrodes and a set of ground electrodes;
   wherein the high conductive density electrode is one of the positive electrodes; and
   wherein the means for electrically connecting the alternating layers of electrodes includes forming an internal connection hole in the plurality of layers and filling the hole with conductive material.

6. A high current multilayer ceramic capacitor comprising:
   a plurality of layers of a ceramic substrate;
   a plurality of electrodes interleaved with intermediate layers of the ceramic substrate;
   a high conductive density electrode formed on an exposed surface of a top or bottom layer of the substrate;
   means for electrically connecting alternating layers of electrodes to form a set of positive electrodes and a set of ground electrodes;
   wherein the high conductive density electrode is one of the positive electrodes; and
   wherein the means for electrically connecting the alternating layers of electrodes includes extending an end of selected positive or ground electrodes to the edges of the ceramic layers and metalizing the exposed edges with a conductive material.

7. The capacitor of claim 6, wherein the ground electrodes are oriented at substantially a right angle to the positive electrodes.

8. A method for forming a multilayer ceramic capacitor comprising the steps of:
   forming a plurality of layers of a ceramic substrate, wherein each layer has an upper and lower surface, and each layer is composed of a heat fusible oxide of ceramic powder;
   depositing layers of heat fusible electrode material on the upper and lower surfaces of intermediate layers of the ceramic substrate to form a composite stack of layers;
   sintering the composite stack of dielectric/electrode layers to form a fused stack;
   forming an electrical connection between alternating layers of electrodes to form a set of positive electrodes and a set of ground electrodes;
   forming a slot on an exposed surface of a top or bottom layer of the fused stack and filling the slot with heat fusible electrode material to form a high conductive density electrode, wherein the high conductive density electrode is one of the positive electrodes; and
   heating the stack to fuse the heat fusible electrode material deposited in the slot.

9. The method of claim 8, further including the steps of forming parallel electrical connections at a set of first ends of the positive electrodes and at a set of second ends of the positive electrodes.

* * * * *